US012653702B2

(12) United States Patent
Laghi et al.

(10) Patent No.: US 12,653,702 B2
(45) Date of Patent: Jun. 16, 2026

(54) ATTACHMENT FOR LOCKING PROSTHETIC LINERS

(71) Applicant: Alps South Europe, S.R.O., Plzen (CZ)

(72) Inventors: Aldo Laghi, Pinellas Park, FL (US); Nathaniel Vint, Palm Harbor, FL (US); Kurt T. Kruger, St. Petersburg, FL (US); Jakob W. McClelland, Gulfport, FL (US)

(*) Notice: Subject to any disclaimer, the term of this patent is extended or adjusted under 35 U.S.C. 154(b) by 488 days.

(21) Appl. No.: 18/237,654

(22) Filed: Aug. 24, 2023

(65) Prior Publication Data

US 2024/0099863 A1 Mar. 28, 2024

Related U.S. Application Data

(63) Continuation-in-part of application No. 18/234,747, filed on Aug. 16, 2023.

(60) Provisional application No. 63/440,736, filed on Jan. 24, 2023, provisional application No. 63/410,294, filed on Sep. 27, 2022.

(51) Int. Cl.
*A61F 2/78* (2006.01)
(52) U.S. Cl.
CPC .... *A61F 2/7812* (2013.01); *A61F 2002/7818* (2013.01)

(58) Field of Classification Search
CPC ............ A61F 2/7812; A61F 2002/7818; A61F 2002/7875; A61F 2/78; A61F 2/80
See application file for complete search history.

(56) References Cited

U.S. PATENT DOCUMENTS

| | | | | |
|---|---|---|---|---|
| 2016/0338858 A1* | 11/2016 | Hurley | ................. | A61F 2/7812 |
| 2019/0125554 A1* | 5/2019 | Krämer | ..................... | A61F 2/80 |
| 2019/0254845 A1* | 8/2019 | Wernke | .................... | A61F 2/72 |
| 2020/0146850 A1* | 5/2020 | Asgeirsson | ........... | A61F 2/7812 |
| 2020/0179140 A1* | 6/2020 | Valois | .................. | A61F 2/7812 |
| 2023/0018244 A1* | 1/2023 | Wernke | ................. | A61B 5/296 |

* cited by examiner

*Primary Examiner* — Nitin Patel
(74) *Attorney, Agent, or Firm* — Cole Carlson

(57) ABSTRACT

A prosthetic liner incorporating a locking attachment that can be used by amputees to engage their prosthetic liner with a prosthetic device. The prosthetic liner has an open proximal end and a closed distal end with a liner opening at the closed distal end. The prosthetic liner further comprises an external fabric layer and an internal elastomer layer. This internal elastomer layer may be made of silicone, urethane, or a thermoplastic styrene-based elastomer gel. The locking attachment is comprised of two parts: an umbrella further comprising a stem having a base and the exterior screw cap. The exterior screw cap can engage the umbrella in a variety of ways including, but not limited to, locking grooves, locking studs, and locking teeth. In addition, the locking attachment has an internally threaded central aperture that allows for the expulsion of air as well as the mounting of a prosthesis.

15 Claims, 5 Drawing Sheets

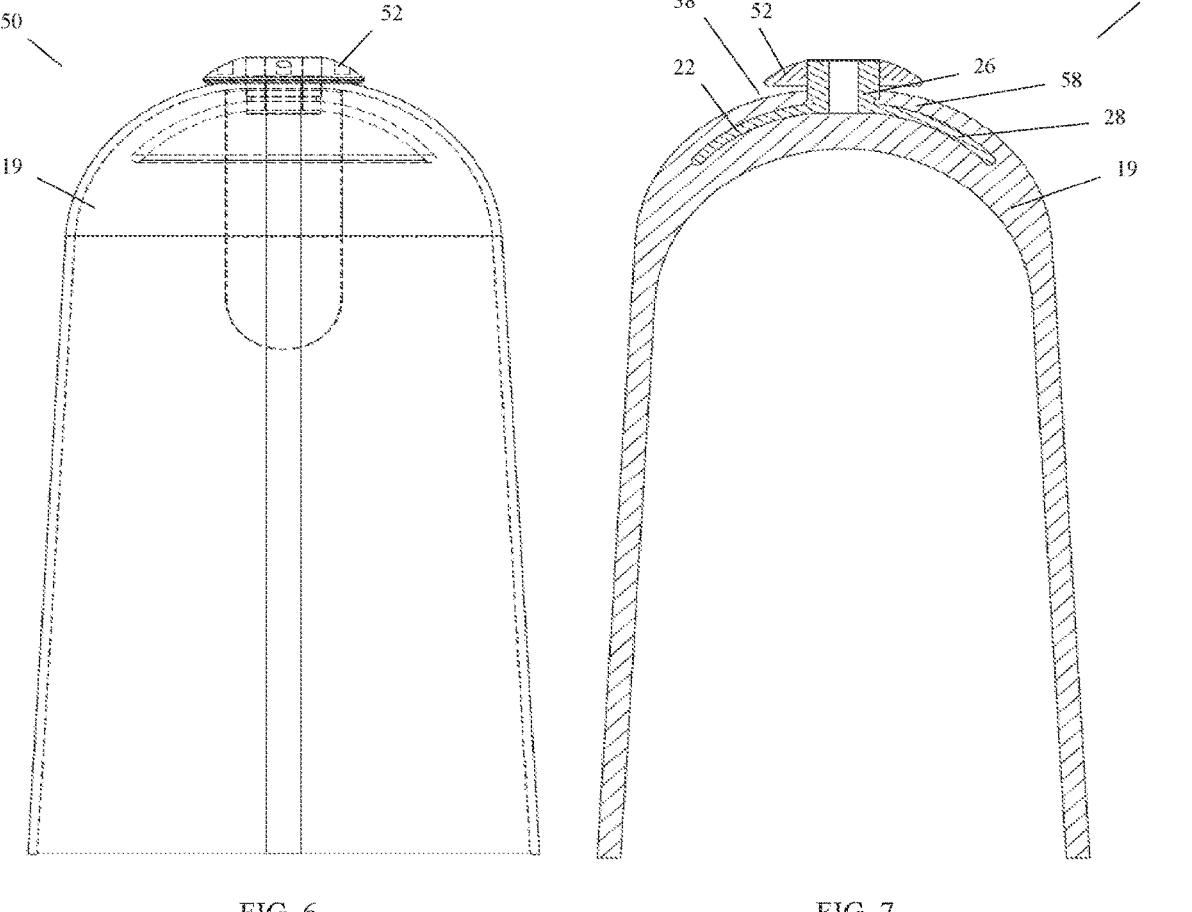
FIG. 6                    FIG. 7

ATTACHMENT FOR LOCKING PROSTHETIC LINERS

CROSS-REFERENCE TO RELATED APPLICATIONS

This application is a continuation-in-part of U.S. application Ser. No. 18/234,747, titled "Novel Attachment for Locking Prosthetic Liners," filed Aug. 16, 2023, which claims priority to U.S. Provisional Application No. 63/410, 294, filed Sep. 27, 2022, and U.S. Provisional Application No. 63/440,736, filed Jan. 24, 2023, the contents of which are incorporated by reference herein in their entirety.

FIELD OF THE INVENTION

This invention relates to liners for use in a prosthetic assembly. Specifically, the described invention relates to liners with a locking attachment for securing to a prosthetic socket to a prosthetic liner.

DESCRIPTION OF BACKGROUND ART

Liners with a distal attachment for a locking system have been used on prosthetic devices for many years. As described in U.S. Pat. No. 6,454,812 to Laghi, one of the co-inventors of the present invention and incorporated herein by reference, this system has to attach in a secure method to the distal portion of the liner to prevent separation or pistoning (the distal distraction of the liner from the residual limb). Many methods of securing a distal portion including adhering using adhesive materials, grommetting, and molding. This could result in locking systems that had an exposed stem that required protection by covering with silicone, gel, or other material unrelated to the locking system itself and which could cause the system as a whole to not be as secure thereby potentially causing separation or pistoning. In addition, prior art systems generally taught that distal umbrellas mounted to an external surface of the fabric of the prosthetic liner.

The primary drawbacks to the prior art are lack of strength and effort. The attachment is only as strong as the bond between the distal umbrella and the fabric. Likewise, additional effort is needed to add a grommet to ensure that the distal umbrella is securely attached to the prosthetic liner. Accordingly, there exists a need for an improved method of securing a distal umbrella to a distal end of a prosthetic liner that does not require the distal umbrella to be embedded in the interior elastomer gel layer or to engage physically with the outer fabric layer. Likewise, prior art liners require destruction of the liner in order to inspect the bonding surfaces.

This present invention relates to the attachment of the locking connection to the distal portion of the liner. The novel screw cap attachment allows the base of the locking attachment to reside within the liner and the exterior screw cap to hold and secure the locking attachment to the fabric portion of the liner before an elastomeric matrix is applied to provide the cushion comfort for the patient. An internal locking attachment of the liner allows for a higher strength and safety for the patient since the locking portion is internal to the body of the prosthetic. Extra elastomeric material can provide comfort over the internal distal attachment portion of the locking attachment.

Therefore, it is an object of this invention to provide an improvement which overcomes the aforementioned inadequacies of the prior art devices and provides an improvement which is a significant contribution to the advancement of the prosthetic assembly art.

Another object of this invention is to provide an improvement over the standard methods of gluing, grommet, and molding to simplify the manufacture while improving the physical strength and aesthetics of the locking liner.

Another object of this invention is to provide an external locking ring that also compresses the exterior fabric into the reinforcing layer ensuring a mated composite structure.

Another object of this invention is to provide a reinforcement that can vary in circumference distally or regionally to provide different levels of strength, stretch, and comfort.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The long-standing but heretofore unfulfilled need for an apparatus that overcomes the limitations of the prior art is now met by a new, useful, and non-obvious invention. The invention meets the need for a new prosthetic locking attachment system that overcomes the issues inherent in the prior art.

The present invention relates generally to a prosthetic liner incorporating a locking attachment that can be used by amputees to engage their prosthetic liner with a prosthetic device. The prosthetic liner has an open proximal end and a closed distal end with a liner opening at the closed distal end. The prosthetic liner further comprises an external fabric layer and an internal elastomer layer. This internal elastomer layer may be made of silicone, urethane, or a thermoplastic styrene-based elastomer gel. The locking attachment is comprised of two parts: an umbrella further comprising a stem having a base and the exterior screw cap. The exterior screw cap can engage the umbrella in a variety of ways including, but not limited to, locking grooves, locking studs, and knurled locking teeth. In addition, the locking attachment has an internally threaded central aperture that allows for the expulsion of air as well as the mounting of a prosthesis.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present disclosure and its advantages, reference is now made to the following descriptions, taken in conjunction with the accompanying drawings, in which:

FIG. 6 is a perspective, partially sectional view of the elastomer layer with umbrella and cap of an alternative embodiment of the present invention;

FIG. 7 is a cross-sectional view of FIG. 6;

Similar reference numerals refer to similar parts throughout the several views of the drawings.

DETAILED DESCRIPTION OF THE DRAWINGS

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Figures 1, 2, 2A:
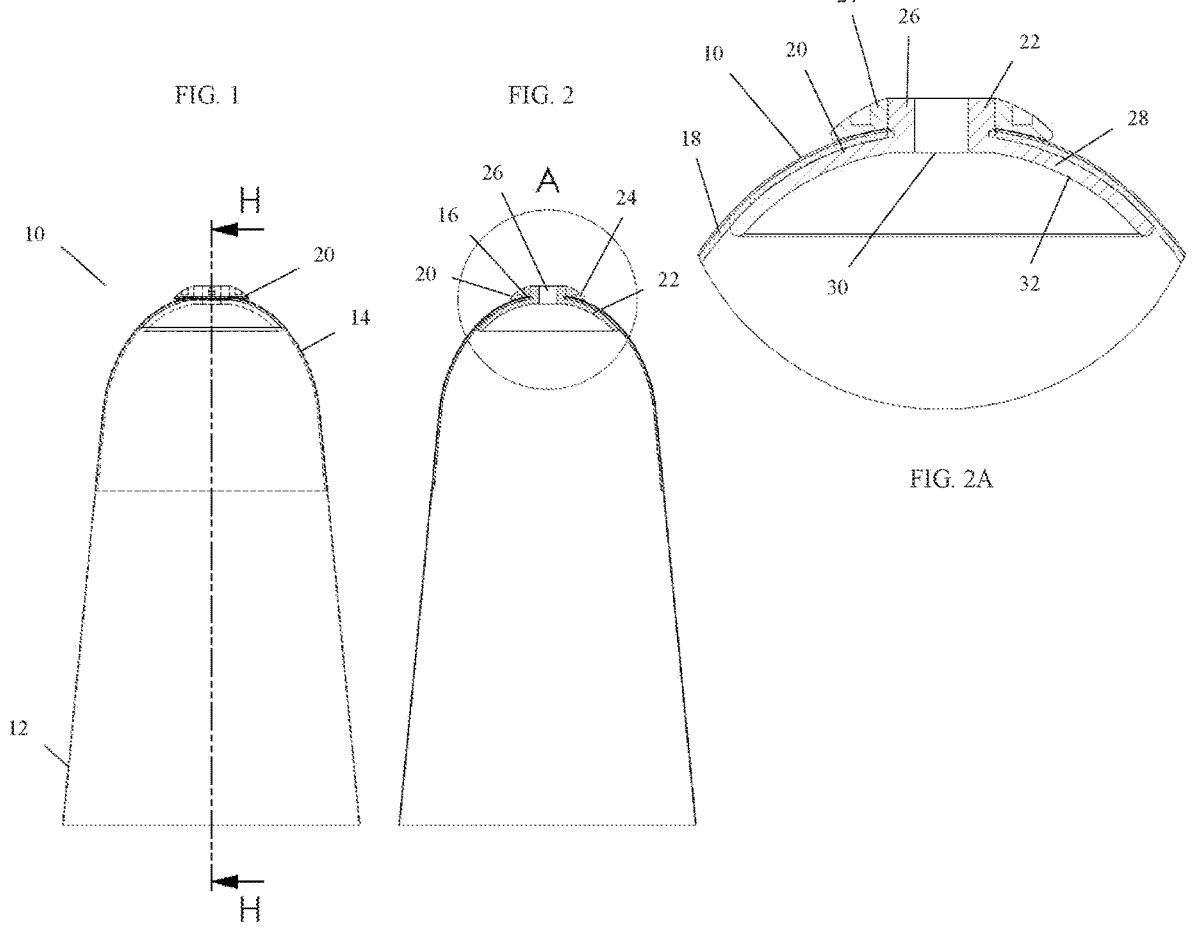
FIG. 1 is a perspective view of a liner implementing the attachment of the present invention.
FIG. 2 is a cross-sectional view of a liner implementing the attachment of the present invention along line H-H of FIG. 1.
FIG. 2A is a magnified view of Section A of FIG. 2.
Figure 3A:
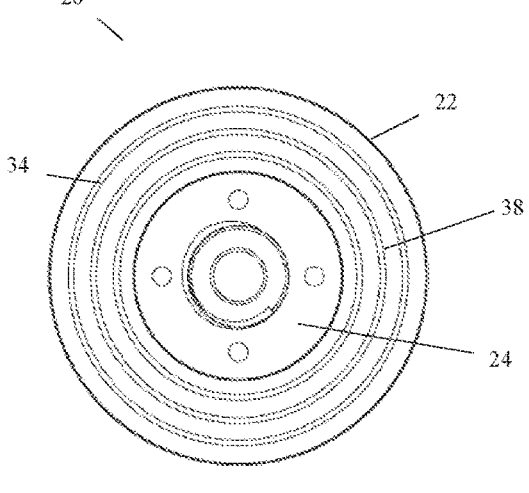
FIG. 3A-3D are perspective views of the attachment cap and umbrella both disengaged and engaged.
Figure 3B:
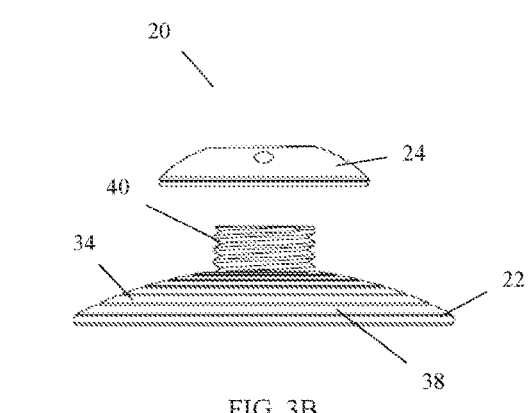
Figure 3C:
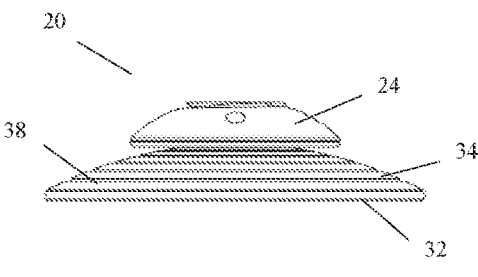
Figure 3D:
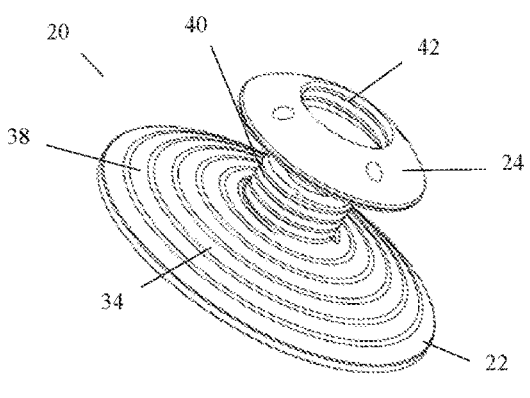

FIGS. 1, 2, and 2A illustrate a preferred embodiment of a prosthetic liner 10 incorporating a locking attachment 20 that can be used by amputees to engage their prosthetic liner 10 with a prosthetic device (not shown). The prosthetic liner 10 has an open proximal end 12 and a closed distal end 14. The prosthetic liner 10 further comprises an external fabric layer 18 and an internal elastomer layer 19 bonded together into a composite material with a liner opening 16 at the closed distal end 14. This internal elastomer layer 19 may be made of silicone, urethane, or a thermoplastic styrene-based elastomer gel. The locking attachment 20 is comprised of two parts: an umbrella 22 further comprising a stem 26 having a base 28 and the exterior screw cap 24. Stem 26 incorporates a plurality of stem threads 40 that engage with screw cap threads 42. The exterior screw cap 24 can engage the umbrella 22 in a variety of ways including, but not limited to, locking grooves, locking studs, and locking teeth. The exterior screw cap 24 preferably uses non-standard threading (i.e. cross-threading), non-standard tooling for installation, or a thread lock to ensure that a patient cannot unscrew the exterior screw cap 24 from the base 28 without assistance from a prosthetist or other qualified individual. Alternatively, the exterior screw cap 24 can be glued to the exterior fabric layer 18 once fully engaged with the stem 26 and base 28 to prevent removal entirely. Welding or staking is also a possibility. In addition, the locking attachment 20 has an internally threaded central aperture 30 that allows for the expulsion of air as well as the mounting of a prosthesis.

As shown in more detail in FIG. 2A, the umbrella 22 curves to the shape of the closed distal end 14 of the prosthetic liner 10. Further, the umbrella 22 is adhered to the internal elastomer layer 19 either chemically or mechanically and, importantly, is not embedded in the elastomer. Nor does the present invention require crimping the external fabric layer 18 to the umbrella 22. The interior face 32 of the base 28 may have an additional layer of elastomer to provide comfort over the internal distal attachment portion of the locking attachment 20. The umbrella 22 and the exterior screw cap 24 are preferably made of the same material and are generally desired to be lightweight materials that can resist wear and tear such as aluminum, stainless steel, titanium, glass-reinforced nylon, composite materials, high temperature ridged plastics, and other similar materials. The umbrella 22 may be a unitary piece of material or may have a plurality of holes machined into the base 28.

As shown in FIGS. 3A-3D, the umbrella 22 of locking attachment 20 preferably includes a plurality of radial grooves 34 on an upper face 38. These grooves 34 allow for an increased surface area for an adhesive such as an epoxy or glue to be applied prior to attaching the umbrella 22 to the interior elastomer layer 19. Alternatively, the umbrella 22 can be attached to an interior side 36 of the external fabric layer 18. Once secured to the prosthetic liner 10, the exterior screw cap 24 can engage with the stem 26 of the umbrella 22. Other alternative arrangements to the radial grooves 34 include randomly placed divots, dimples, linear grooves extending outward from the stem 26, or any other arrangement that creates an increased surface area for an adhesive to provide increased grip.

One of the main benefits of this arrangement is that manufacturing time is greatly reduced. Further, less equipment is needed since no mandrels are required for grommetting the locking mechanism onto the prosthetic liner. In addition, the present invention allows for the non-destructive inspection of bonding surfaces between the exterior fabric layer 18 and the internal elastomer layer 19 given that the exterior screw cap 24 can be disengaged from the base 28 by a prosthetist having the correct tools. Furthermore, the present invention allows for set manufacturing specifications as it will be known at exactly what pressure the exterior screw cap 24 should be attached to the base 28 such that the prosthetic liner 10 and the locking attachment 20 are mechanically attached to one another.

Figures 4, 5, 5A:
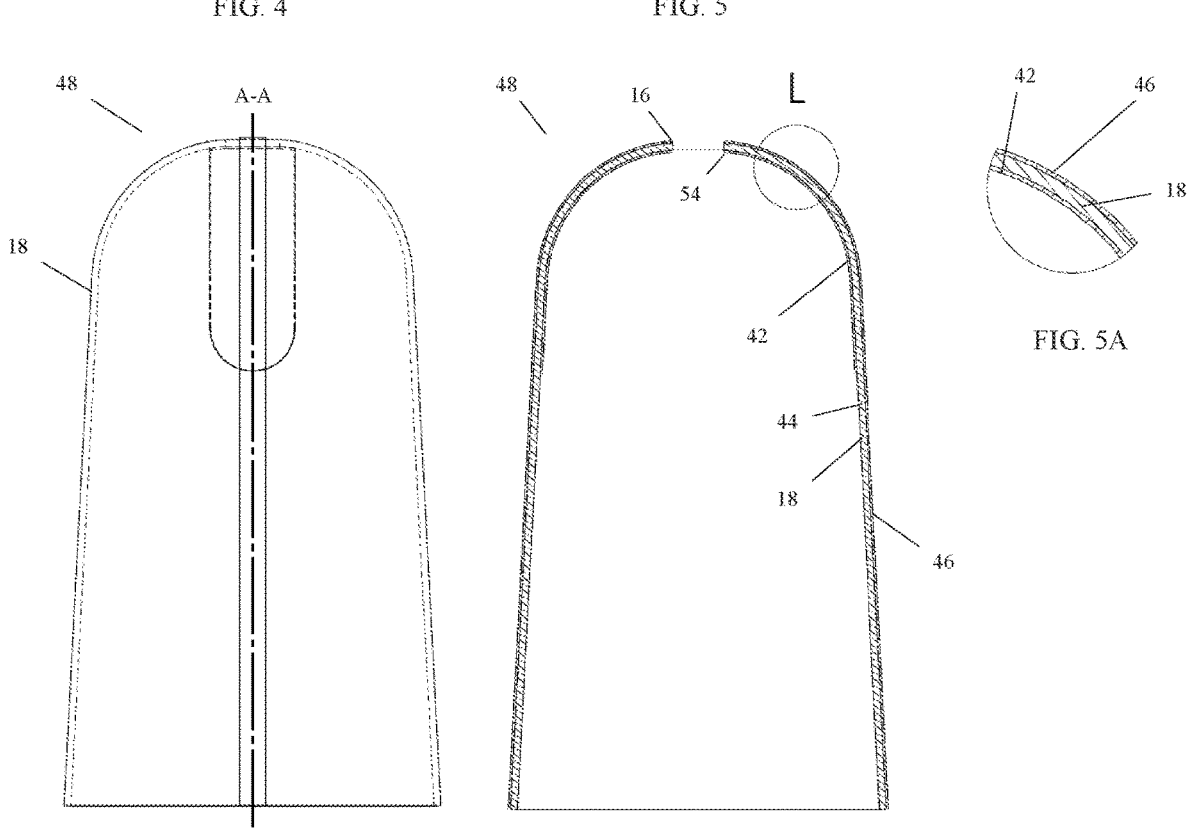
FIG. 4 is a cross-sectional view of the outer fabric layer of an alternative embodiment of the present invention.
FIG. 5 is a cross-sectional view of FIG. 4 along line A-A.
FIG. 5A is a magnified view of detail L from FIG. 5.
Figures 8, 9, 9A:
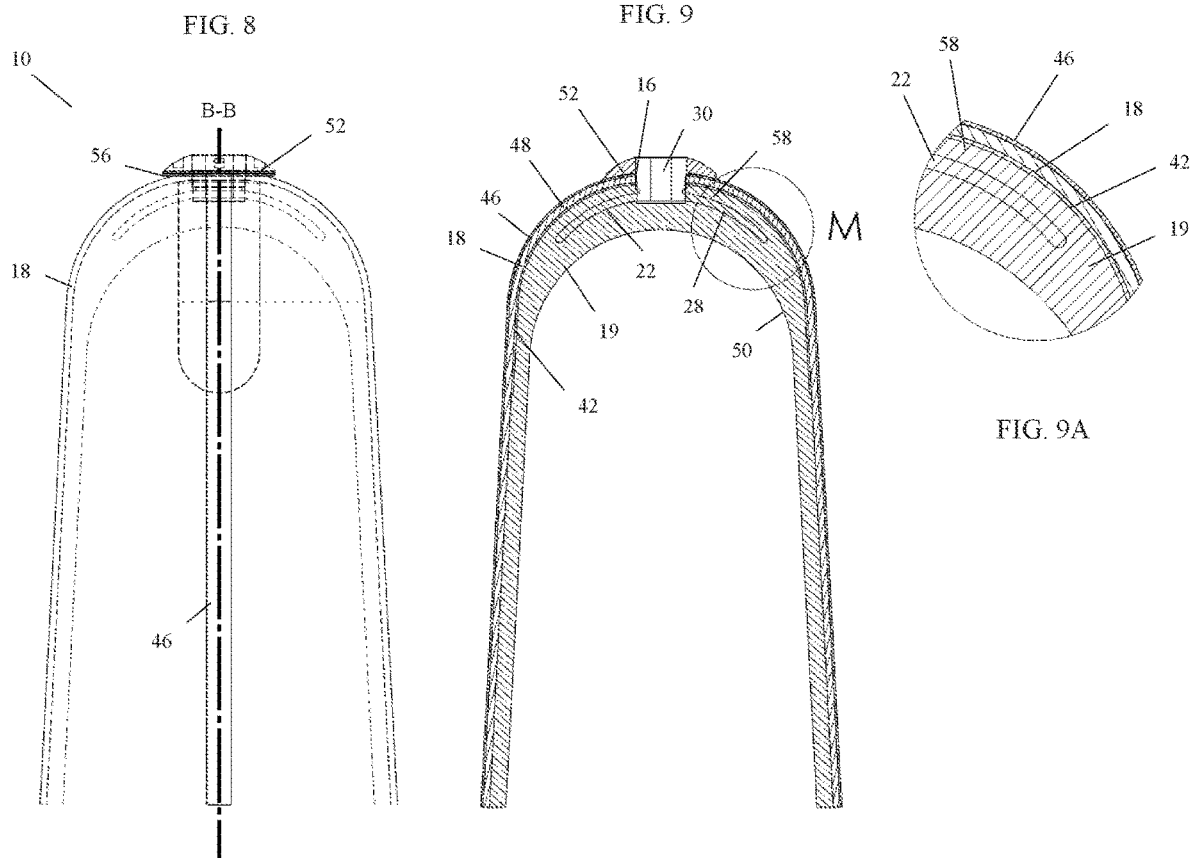
FIG. 8 is a perspective, partially sectional view of the full assembly of an alternative embodiment of the present invention.
FIG. 9 is a cross-sectional view of FIG. 8 along line B-B.
FIG. 9A is a magnified view of detail M from FIG. 9.

An alternative embodiment is provided in FIGS. 4-9A. In this embodiment, as seen in FIGS. 4-5A, the external fabric layer 18 has an internal support strip 42 at the closed distal end 14. The internal support strip 42 is generally glued to an internal fabric face 44 of the external fabric layer 18 but may be attached by any known means and only extends up to five inches from the closed distal end 14 towards the open proximal end 12. The internal support strip 42 also has a support strip opening 54 in the same location as the liner opening 16 to allow for the stem 26 of the umbrella 22 to interface with an exterior cap 52. External fabric layer 18 further includes an external fabric tape 46 that extends the length of the external fabric layer 18 which, when assembled prior to molding with internal elastomer gel layer 19, creates a fabric complex 48. As seen in FIGS. 6-7, the umbrella 22 is molded into the internal elastomer gel layer 19 with the stem 26 extending through an outer elastomer face 38 with an elastomer layer 58 above the base 28 of the umbrella 22 thereby forming an elastomer complex 50. When the elastomer complex 50 is formed into a composite 60 with external fabric complex 48 (whether through heating, gluing, or other means), as shown in FIGS. 8-9A, exterior cap 52 engages with the stem 26 that is extending through liner opening 16 and support strip opening 54. The exterior cap 52 can engage with the stem 26 through the use of a grommet 56 but may also engage using other conventional means such as those described in the previous embodiment or through the use of a shelf or other threading means to prevent wrinkling or movement of the external fabric complex 48 at the liner opening 16 when the exterior cap 52 is added for engagement. The additional elastomer layer 58 above the base 28 provides additional comfort to the user and allows for some slight shifting of the umbrella 22 when in use by a user based on shifting weight.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A prosthetic liner comprising:

a substantially tubular fabric covering having an open proximal end, a closed dome-shaped distal end, and an internal elastomer layer, wherein the closed dome-shaped distal end further comprises a liner opening;

an internal support strip extending from the closed distal end located on an interior face of the fabric covering;

an external fabric tape extending from the open proximal end to the closed dome-shaped distal end of the fabric covering, wherein the fabric covering, internal support strip, and external fabric tape form a fabric complex;

a elastomer complex comprising a locking attachment molded into an elastomer, wherein the locking attachment further comprises an umbrella, wherein the umbrella further comprises a stem and a base and wherein the stem extends through an outer elastomer face and the liner opening;

wherein the fabric complex and the elastomer complex form a composite and wherein an exterior cap engages with the stem.

2. The prosthetic liner of claim 1 wherein the base of the umbrella is dome-shaped to correspond to the dome-shaped distal end.

3. The prosthetic liner of claim 1 wherein the umbrella and the exterior screw cap comprise aluminum.

4. The prosthetic liner of claim 1 wherein the internal elastomer layer comprises silicone.

5. The prosthetic liner of claim 1 wherein the internal elastomer layer comprises a thermoplastic styrene-based elastomer gel.

6. The prosthetic liner of claim 1 wherein the exterior screw cap further engages the stem with locking teeth and a thread lock.

7. The prosthetic liner of claim 1 wherein the base further comprises a plurality of radial grooves on an upper face.

8. The prosthetic liner of claim 1 wherein the base further comprises a plurality of dimples on an upper face.

9. The prosthetic liner of claim 1 wherein the base further comprises a plurality of randomly placed divots on an upper face.

10. The prosthetic liner of claim 1 wherein the umbrella is not embedded in the internal elastomer layer.

11. The prosthetic liner of claim 1 wherein the umbrella and the exterior screw cap do not crimp the fabric covering once engaged.

12. The prosthetic liner of claim 1 wherein the central aperture is internally threaded.

13. The prosthetic liner of claim 1 wherein the exterior cap further engages a grommet above the fabric covering.

14. A prosthetic liner comprising:

a substantially tubular fabric covering having an open proximal end, a closed dome-shaped distal end, and an internal elastomer layer, wherein the closed dome-shaped distal end further comprises a liner opening;

an internal support strip extending from the closed dome-shaped distal end located on an interior face of the fabric covering wherein the fabric covering and internal support strip form a fabric complex;

an elastomer complex comprising a locking attachment molded into an elastomer, wherein the locking attachment further comprises an umbrella, wherein the umbrella further comprises a stem and a base and wherein the stem extends through an outer elastomer face and the liner opening;

wherein the fabric complex and the elastomer complex form a composite and wherein an exterior cap engages with the stem.

15. A prosthetic liner comprising:

a substantially tubular fabric covering having an open proximal end, a closed dome-shaped distal end, and an internal elastomer layer, wherein the closed dome-shaped distal end further comprises a liner opening;

an internal support strip extending from the closed dome-shaped distal end located on an interior face of the fabric covering wherein the fabric covering and internal support strip form a fabric complex;

an elastomer complex comprising a locking attachment molded into an elastomer, wherein the locking attachment further comprises an umbrella, wherein the umbrella further comprises a stem and a base and wherein the stem extends through an outer elastomer face and the liner opening;

wherein the fabric complex and the elastomer complex form a composite and wherein an exterior cap engages with the stem.

* * * * *